(12) United States Patent
Patel

(10) Patent No.: US 10,702,469 B2
(45) Date of Patent: Jul. 7, 2020

(54) NON-AQUEOUS TOPICAL SOLUTION OF DICLOFENAC AND PROCESS FOR PREPARING THE SAME

(75) Inventor: Ketan R. Patel, Ahmedabad (IN)

(73) Assignee: TROIKAA PHARMACEUTICALS LTD., Gujarat (IN)

( * ) Notice: Subject to any disclaimer, the term of this patent is extended or adjusted under 35 U.S.C. 154(b) by 1163 days.

(21) Appl. No.: 12/451,918

(22) PCT Filed: Jun. 9, 2008

(86) PCT No.: PCT/IN2008/000363
§ 371 (c)(1),
(2), (4) Date: Dec. 7, 2009

(87) PCT Pub. No.: WO2009/047785
PCT Pub. Date: Apr. 16, 2009

(65) Prior Publication Data
US 2010/0120918 A1    May 13, 2010

(30) Foreign Application Priority Data
Jun. 8, 2007   (IN) .......................... 1092/MUM/2007

(51) Int. Cl.
*A61K 31/196* (2006.01)
*A61K 9/00* (2006.01)
*A61K 9/08* (2006.01)

(52) U.S. Cl.
CPC .............. *A61K 9/0014* (2013.01); *A61K 9/08* (2013.01); *A61K 31/196* (2013.01)

(58) Field of Classification Search
CPC ..... A61K 9/0014; A61K 31/196; A61K 47/10
See application file for complete search history.

(56) References Cited

U.S. PATENT DOCUMENTS

| | | |
|---|---|---|
| 4,353,896 A | 10/1982 | Levy |
| 4,652,557 A | 3/1987 | Sandborn |
| 4,704,406 A | 11/1987 | Stanislaus et al. |
| 4,933,184 A | 6/1990 | Tsuk |
| 5,093,133 A | 3/1992 | Wisniewski et al. |
| 5,318,960 A | 6/1994 | Toppo |
| 5,654,337 A | 8/1997 | Snyder, II |
| 5,665,378 A | 9/1997 | Davis et al. |
| 5,976,566 A * | 11/1999 | Samour ................ A61K 9/0014 424/449 |
| 5,985,860 A | 11/1999 | Toppo |
| 6,054,484 A | 4/2000 | Sekine et al. |
| 6,193,996 B1 | 2/2001 | Effing et al. |
| 7,026,360 B1 | 4/2006 | Festo |
| 2003/0082226 A1* | 5/2003 | Samour et al. ............... 424/449 |
| 2004/0146548 A1* | 7/2004 | Takada ................ A61K 9/7076 424/449 |
| 2007/0196453 A1* | 8/2007 | Zhang ................. A61K 9/7015 424/443 |

FOREIGN PATENT DOCUMENTS

WO    9857624    12/1998

OTHER PUBLICATIONS

Parsaee et al.; "In-vitro release of diclofenac diethylammonium from lipid-based formulations"; 2002; International Journal of Pharmaceutics; 241; 185-190.*
Kogan et al (Advances in Colloid and Interface Science, 2006; 123-126:369-385).*
Trommer et al (Skin Pharmacol Physiol, 2006; 19:106-121).*
Robert, M and Walker, M, "Water—The Most Natural Penetration Enhancer", in: Walters KA, Hadgraft J(eds), Skin Penetration Enhancement, 1993, New York: Marcel Dekker, p. 1-30.
Minghetti, P et al, "Ex Vivo Study of Transdermal Permeation of Four Diclofenac Salts from Different Vehicles", J Pharm Sci, 2007; 96(4); 814-23.
Nishihata, T et al, "Percutaneous absorbtion of diclofenac in rats and humans: aqueous gel formulation", Int J Pharm, 1988; 46; 1-7.
Ho Ho et al, "The Influence of Cosolvents on the In-vitro Percutaneous Penetration of Diclofenac Sodium from a Gel System", J Pharm Pharmacol, 1994; 46; 636-42.
International Search Report for WO 2009/047785 A3.

* cited by examiner

Primary Examiner — Marcos L Sznaidman
Assistant Examiner — Rayna Rodriguez
(74) Attorney, Agent, or Firm — Baker & Hostetler LLP

(57) ABSTRACT

A non-aqueous topical solution composition of pharmaceutically acceptable salt of diclofenac is disclosed. The non-aqueous topical solution composition comprises therapeutically effective amount of pharmaceutically acceptable salt of diclofenac, solublizer, penetration enhancer and solvent, and optionally a humectant, counter irritant, additional penetration enhancer and anti-oxidants and a process for preparing the same.

3 Claims, No Drawings

NON-AQUEOUS TOPICAL SOLUTION OF DICLOFENAC AND PROCESS FOR PREPARING THE SAME

CROSS REFERENCE TO RELATED APPLICATIONS

This application is a National Phase entry of International Patent Application Serial No. PCT/IN2008/000363 filed 9 Jun. 2008, and claims the benefit of priority of Indian Patent Application No. 1092/MUM/2007 filed 8 Jun. 2007, which are hereby incorporated by reference.

FIELD OF THE INVENTION

In general, this invention relates to a novel topical composition of diclofenac. More particularly, the present invention provides a non-aqueous topical solution composition comprising a pharmaceutically acceptable salt of diclofenac and the process for preparing the same.

BACKGROUND OF THE INVENTION

The development of novel or improved dosage forms and delivery system for therapeutically active drugs has been and will continue to be the subject of research and development for both existing and novel drugs. More often, a particular delivery system delivers excessive amount of drug than is actually required, which leads to increased concentration of drug in blood plasma and is responsible for their respective side effects. The reasons for such theoretically excessive doses are many and include, inter alia, the mode of administration of the physiologically active ingredients.

The recent investigations with respect to transdermal or topical drug delivery system have increased resulting in a number of commercially viable products for the administration of various physiologically active anti-inflammatory agents with enhanced bioavailability and absorption. Diclofenac is one such anti-inflammatory and analgesic used widely in the pain management. Diclofenac and its pharmaceutically acceptable salts are presented most commonly in the form of tablets, injectables, gels and recently as clear aqueous solution for topical use. When orally administered diclofenac preparations are known to produce GI side effects. Research and development work has been conducted on topical dosage forms of diclofenac with a view of offering localized action at site of pain through various topical delivery systems.

Robert, S. M and Walker M (1993, In Pharmaceutical Skin Penetration Enhancement, 1-30) disclosed that the permeability of the pharmaceutical active ingredient is increased in presence of water due to hydration of the skin and solvation of the intercellular lipids. One of the proposed mechanisms for the facilitation of transport is by water being absorbed into the stratum corneum where it acts as a plasticizer in its bound state. In view of above theories, all topical preparations of diclofenac salts, like creams, gels, lotions and solutions is manufactured using water as an essential component with the objective of aiding permeation of the active drug.

The ex-vivo investigations by Minghetti, P. et.al. J. Pharm. Sci. 2007, April; 96(4):814-23 revealed that aqueous formulations containing diclofenac salt with an organic base appear to be the best combination to, promote permeation in topical applications. Wherein, the studies were carried out employing human skin for different diclofenac salts viz. sodium, potassium, diethylamine and epolamine and solvents viz. water, propylene glycol, oleic acid and transcutol.

In one another investigation, Nishihata, T. et al. Int. J. Pharm.; 1988; 46; 1-7 revealed that the rat dorsal percutaneous absorption of sodium diclofenac increased with an increase in sodium diclofenac concentration in an applied aqueous solution, but the bioavailability was poor. Further, the addition of 10% w/w ethanol in the aqueous solution containing sodium diclofenac apparently increased the percutaneous absorption of diclofenac and it was attributed to the increase in the sodium diclofenac concentration present in the applied solution. Further, the teachings by Ho Ho, et. al. J. Pharm. Pharmacol. 1994; 46; 636-42 disclosed that maximal penetration rate was found in a vehicle containing water and ethanol in a ratio of 3:1.

U.S. Pat. No. 4,353,896 describes a penetration of topical medicament useful in treating athletic injuries or other painful subdermal conditions. Wherein, the formulation is an aqueous based dosage form containing hydrocortisone, DMSO, methyl salicylate and alcohol.

U.S. Pat. No. 4,933,184 describes aqueous formulations containing menthol that produce enhanced transdermal drug delivery.

U.S. Pat. No. 4,652,557 describes pharmaceutical solutions containing active pharmaceutical ingredients, including diclofenac, in a solution comprising DMSO as penetration enhancer along with glycerol, propylene glycol and water.

U.S. Pat. No. 7,026,360 discloses pharmaceutical compositions containing non steroidal anti-inflammatory drugs including diclofenac with enhanced absorption of active ingredients. Phosphatidylcholine is used for the enhancement of absorption of active ingredients. The enhancement of absorption of active ingredient is sought by incorporation of 0.1% -20% by weight of phosphatidylcholine.

U.S. Pat. No. 5,093,133 teaches about the method for preparing hydro alcoholic gel of ibuprofen for percutaneous delivery. Wherein, the gel comprises ibuprofen along with alcohol, non-volatile solvent, gelling agents, sufficient base and water.

U.S. Pat. No. 5,318,960 and 5,985,860 describes a composition for transdermal delivery of pain relieving NSAID's like ibuprofen, methotrexate, capsaicin, diphenhydramine, methylnicotinate, indomethacin, ketoprofen, aspirin, diclofenac sodium, etc. and combinations thereof. The compositions are manufactured by mixing an appropriate amount of surfactant and co-solubilizer i.e. alcohol to establish a non-aqueous phase. There after, an appropriate amount of distilled water is slowly added to form a clear oil continuous solution.

U.S. Pat. No. 5,654,337 relates to a composition of pharmaceutically active substance including anti-inflammatory agent in a formulation, which is rapidly absorbed through the skin. The formulation comprises a polar lipid like lecithin, surfactant, water and urea with a pH of about 6-8.

U.S. Pat. No. 6,054,484 describes about the transparent aqueous solution of diclofenac sodium dissolved in a solvent mixture of a fatty acid dialkylolamide and water. The aqueous solution is claimed to have higher penetration.

U.S. Pat. No. 6,193,996 describes a pressure sensitive skin adhesive for transdermal delivery of diclofenac. The formulation incorporates effective amount of diclofenac or its pharmaceutically acceptable salts in the mixture of adhesives with penetration enhancer.

WO9857624 teaches about an invention relating to pharmaceutical preparation for topical application containing alcohol along with short chain n-alkylpyrolidone and at least one pyrolidone substituted with long chain alkyl radical with sufficient quantity of water.

U.S. Pat. No. 5,665,378 states the use of formulations containing capsaicin and pamabrom to alleviate pain. The aqueous formulations are used either as patches or in the form of creams.

U.S. Pat. No. 4,704,406 discloses a non-aqueous solution composition of arylalkanoic acid or its salts as sprayable liquids. This objective is achieved by using a two component carrier system comprising volatile and non-volatile solvents and wherein the concentration of the volatile solvents (ethanol, isopropyl alcohol and propanol) is high as compared to the non-volatile solvents. Accordingly, the ratio of volatile to the non-volatile solvent range is range of 1:1 to 20:1 by weight. The essential features of this invention are to provide the rapid cooling and film formation at the site of application, through fast evaporation of volatile solvent.

Diclofenac or its pharmaceutically acceptable salts and other NSAIDs produce their anti-inflammatory analgesic action through inhibition of prostaglandin synthesis. On the other hand, counter irritants like menthol and methyl salicylate produce the sensation of heat at the site of application due to the increased blood circulation in the tissue. Keeping in view the diverse mechanism of action of diclofenac and counter irritants, combination of diclofenac or its pharmaceutically acceptable salts with counter irritants have been also formulated in the form of creams, gels and aerosols to take advantage of the diverse mechanisms of action of diclofenac and counter irritants. This mechanism of action helps to alleviate the pain and inflammation. All these preparations of pharmaceutically acceptable salts of diclofenac with counter irritants reported in the prior arts incorporate water as an essential component of the formulation.

Further it is obvious from the prior art that every inventor has focused on achieving penetration enhancement through use of one or more penetration enhancers and presenting them in one or more of the above dosage forms viz. creams, gels, aerosols, lotion, emulsions, aqueous solutions and non-aqueous solutions. Unfortunately, none of the prior art discloses about the choice of desired dosage form suitable for the salt of diclofenac through topical delivery with enhanced penetration and bioavailability.

In most of the inventions, inventors has tried one or more of a dosage forms for a given transdermal composition, wherein, it is apparent that inventors are certain about the requirement of the nature of the dosage form needed for the enhanced transdermal penetration and hence he/she attempts to prepare one or more of the dosage forms for a single composition. Moreover, the inventions that have disclosed about multiple dosage forms for a single composition have not disclosed any evidence for their superiority among the dosage forms designed, by comparing those dosage forms with the market available products.

Amongst predominantly large number of the topical solutions with enhanced transdermal absorption disclosed in the prior art, a majority of topical solutions use water as one of the essential ingredient in the vehicle with the object of attaining higher transdermal penetration through hydration of the stratum corneum. More particularly, water is used for its solubilizing property. Typical creams are prepared by dissolving water soluble ingredients in the aqueous phase and the oil soluble ingredients in the oily phase. The two phases are mixed along with suitable surfactant to form a cream. In case of aqueous solutions, water is used along with other co solvents and surfactants to solublize the water-soluble ingredients of the formulation and also as a hydrating agent for the skin and in some cases water also helps to reduce the viscosity if the solution.

Further, the non-aqueous topical solutions disclosed in the U.S. Pat. No. 4,704,406 exclude water since the inherent nature of the formulations does not justify the use of water in the formulation. The main objectives of these patents are to provide the rapid cooling and quick film formation at the site of application through evaporation of the solution present in the disclosed sprayable topical solution.

Therefore, there exists a need to formulate a stable, non-toxic, low viscous, non-aqueous, non-greasy topical formulation of pharmaceutically acceptable salt of diclofenac with an enhanced penetration of diclofenac into the skin at the site of application of said topical formulation.

SUMMARY OF THE INVENTION

It is a principal aspect of the present invention to provide a non-aqueous, non-greasy, low viscous, non-irritating and non-dehydrating topical solution comprising pharmaceutically acceptable salt of diclofenac, which exhibits enhanced transdermal penetration resulting in higher blood plasma levels of said drug.

Another aspect of the present invention is to provide a non-aqueous topical solution with enhanced penetration, absorption and bioavailability.

Further aspect of the present invention is to provide a non-aqueous topical solution of pharmaceutically acceptable salt of diclofenac along with pharmaceutically acceptable additives.

The above and other aspects are achieved in accordance with following embodiments. However, the present invention is not limited to the preferred embodiments described herein below.

In accordance with one embodiment of the present invention, there is provided a non-aqueous topical solution comprising effective amount of pharmaceutically acceptable salt of diclofenac preferably in the range of about 1.16% to about 5% w/v and more preferably in the range of about 1.16% to about 2.32% w/v.

In accordance with another embodiment of the present invention, there is provided a non-aqueous topical solution of diethylamine salt of diclofenac along with pharmaceutically acceptable additives.

In accordance with one other embodiment of the present invention, there is provided a novel composition of non-aqueous topical solution comprising an effective amount of pharmaceutically acceptable salt of diclofenac, about 10 to 30% v/v of lower chain alcohol as penetration enhancer and solublizer, a solvent selected from propylene glycol, glycofurol or mixture thereof and optionally a humectant, antioxidant and an additional penetration enhancer. Wherein said lower chain alcohol is having carbon chain length of $C_2$-$C_5$ as penetration enhancer and solublizer, and wherein preferred lower chain alcohol is ethanol in an amount of about 10 to 20% v/v.

In accordance with yet another embodiment of the present invention, there is provided a novel composition of non-aqueous topical solution comprising an effective amount of pharmaceutically acceptable salt of diclofenac, about 10 to 30% v/v of lower chain alcohol as penetration enhancer and solublizer, a solvent selected from propylene glycol, glycofurol or mixture thereof, one or more counter irritants and optionally a humectant, antioxidant and an additional penetration enhancer. Wherein said lower chain alcohol is having carbon chain length of $C_2$-$C_5$ as penetration enhancer and solublizer, and wherein preferred lower chain alcohol is ethanol in an amount of about 10 to 20% v/v.

In accordance with still another embodiment of the present invention there is provided a non-aqueous topical solution composition, wherein said composition is prepared by a process comprising the steps of (a) preparing a solution of therapeutically effective amount of pharmaceutically acceptable salt of diclofenac in the solvent, (b) preparing a solution of penetration enhancer and solublizer, (c) optionally adding an additional penetration enhancer in the resulting solution of step (b), (d) adding, under constant stirring, the solution obtained in step (c), to the solution of step (a), (e) optionally adding a humectant to the resulting solution of step (d) to obtain clear transparent homogenous solution, and (f) adding a sufficient quantity of solvent to make up the volume of the composition up to 100%.

In accordance with another embodiment of the present invention there is provided a non-aqueous topical solution composition, wherein said composition is prepared by a process comprising the steps of (a) preparing a solution of therapeutically effective amount of pharmaceutically acceptable salt of diclofenac in the solvent, (b) preparing a solution of counter-irritant employing a solublizer, (c) optionally adding an additional penetration enhancer and antioxidant in the solution obtained in step (b), (d) adding, under constant stirring, the solution obtained in step (c) to the solution of step (a) to obtain clear transparent homogenous solution, and (e) adding a sufficient quantity of solvent to make up the volume of the composition up to 100%.

DETAILED DESCRIPTION OF THE INVENTION

While this specification concludes with claims particularly pointing out and distinctly claiming that, which is regarded as invention, it is anticipated that the invention can be more readily understood through reading the following detailed description of the invention and study of the included examples.

According to the present invention, the non-aqueous topical solution of pharmaceutically acceptable salt of diclofenac is disclosed. The topical solution composition is non-greasy, non-irritating and non-dehydrating when applied on the skin of a mammal. Further the topical solution exhibits enhanced transdermal penetration resulting in higher blood plasma levels of pharmaceutically acceptable salt of diclofenac than any other existing formulation known in the prior art.

Further, the therapeutically effective amount of pharmaceutically acceptable salt of diclofenac is employed for the preparation of topical solution composition along with various pharmaceutically acceptable additives, wherein, the therapeutically effective amount of salt of diclofenac is in the range of about 1.16% to about 5% w/v and more preferably in the range of about 1.16% to about 2.32% w/v.

The term "therapeutically effective amount" as herein used is the amount or quantity of an active ingredient which is sufficient to elicit the required or desired therapeutic response.

The term "pharmaceutically acceptable additive" as used herein is intended to denote any material, which substantially provides any prophylactic and/or therapeutic enhancement of the present pharmaceutical composition or the employed additive may be inert. Such an additive is added with the purpose of making it possible to obtain a pharmaceutical composition, which has acceptable technical properties and enhanced bioavailability.

According to the present invention, the pharmaceutically acceptable additives employed to prepare the topical solution of salt of diclofenac is selected from solublizer, penetration enhancer, solvent, counter irritant, humectant, antioxidant and so forth.

The counter irritant employed in the present invention is preferably selected from the group comprising methyl salicylate, capsaicin, menthol, oil of wintergreen, camphor, eucalyptus, mustard plasters and turpentine oil and more preferably selected from methyl salicylate, menthol, capsaicin and camphor.

The term "optional" or "optionally" or "with or without" means that subsequently described additives or circumstances may or may not be present, so that the description includes instances where the excipients or circumstances may or may not be present.

The phrase "pharmaceutically-acceptable salts" as used herein refers to non-toxic salts of the compound of the present invention which are generally prepared by reacting free acid with a suitable organic or inorganic base, or which are prepared by reacting free base with a suitable acid. Representative salts include the alkali metal salts such as alkyl or dialkyl amine derivatives, sodium, potassium and alkaline earth salts such as calcium and magnesium. Preferably employed salt of diclofenac for the preparation of said topical solution of salt of diclofenac is diethylamine salt of diclofenac.

Suitable pharmaceutically acceptable solublizer employed for the preparation of topical solution of diclofenac is selected from the group comprising lower chain alcohol having carbon chain length of $C_2$ to $C_5$, more preferably selected from the group comprising ethanol, propanol and isopropanol. The preferable solublizer ethanol is in the range of about 10 to 30% v/v, more preferably 10 to 20% v/v and most preferably 10% v/v, wherein ethanol also serves as an effective penetration enhancer to enhance the bioavailability of the topical solution of diethylamine salt of diclofenac. The solublizer or penetration enhancer used herein is free of water.

The additional penetration enhancer used herein is selected from group comprising saturated and unsaturated long chain fatty acids, ester thereof, alkyl substituted nitrogen containing heterocyclic compounds alone or in combination thereof and more preferably selected from oleic acid, isopropyl myristate, isopropyl palmitate, N-methyl-pyrrolidone (NMP), 2-methyl-pyrrolidone or 1-methyl pyrrolidone alone or combination thereof. The additional penetration enhancer such as oleic acid is employed, preferably in the range of about 1 to about 5% w/v.

The humectant used herein added optionally in the composition of pharmaceutically acceptable salt of diclofenac is selected from the group comprising glycerin, propylene glycol, glyceryl triacetate, polyols, polymeric polyols, lactic acid, urea, alone or mixture thereof and more preferably selected from glycerol and/or urea, alone or in combination thereof. The humectant is used in the concentration of about 2 to about 5% w/v.

The solvent employed to make up the volume of the non-aqueous topical solution composition is preferably selected from the group comprising ether derivative of polyethylene glycol or alkane diols and more preferably selected from glycofurol or propylene glycol, alone or in combination thereof.

Further, it is surprisingly found in our investigations that non-aqueous topical solution of pharmaceutically acceptable salts of diclofenac provide enhanced transdermal absorption and increased blood levels of diclofenac as compared to the aqueous formulations of pharmaceutically acceptable salts of diclofenac. The enhanced transdermal absorption is directly related to its increased quantity of diclofenac absorbed as compared to any other conventional dosage forms.

The enhanced bioavailability and penetration of topical solution of pharmaceutically acceptable salt of diclofenac is characterized by superior analgesic action at the site of application. The superior bioavailability is evaluated by various pharmacokinetic parameters including but not limited to increased values of AUC and $C_{max}$.

The term "$C_{max}$" as used herein refers to the maximum concentration of diclofenac or its pharmaceutically acceptable salt in plasma/blood achieved after topical administration of the said composition.

The term "AUC" (Area Under the Curve) as used herein indicates the total amount of diclofenac or its pharmaceutically acceptable salt absorbed by the blood stream in a predetermined time, generally 24 hours. AUC is a measure of bioavailability and is calculated by integrating plasma concentration levels of salt of diclofenac with respect to time.

The typical non-aqueous topical solution composition of pharmaceutically acceptable salt of diclofenac is disclosed as Type-I and Type-II. Wherein the Type-I is novel composition of non-aqueous topical solution comprising:

(a) an effective amount of pharmaceutically acceptable salt of diclofenac;
(b) about 10 to 30% v/v of lower chain alcohol as penetration enhancer and solublizer;
(c) a solvent selected from propylene glycol, glycofurol or their mixture thereof; and
(d) optionally a humectant, antioxidant and an additional penetration enhancer.

The distinctive Type-II is another novel composition of non-aqueous topical solution comprising:

(a) an effective amount of pharmaceutically acceptable salt of diclofenac;
(b) at least one or more counter irritant;
(c) about 10 to 30% v/v of lower chain alcohol as penetration enhancer and solublizer;
(d) a solvent selected from propylene glycol, glycofurol or their mixture thereof; and
(e) optionally a humectant, antioxidant and an additional penetration enhancer.

The process for preparing Type-I composition is comprising the steps of a) preparing a solution of pharmaceutically acceptable salt of diclofenac in the solvent, b) preparing a solution of penetration enhancer and solublizer, c) optionally adding an additional penetration enhancer in the resulting solution of step (b), d) adding, under constant stirring, the solution obtained in step (c), to the solution of step (a), e) optionally adding a humectant to the resulting solution of step (d), and f) adding a sufficient quantity of solvent to make up the volume of the composition up to 100%.

The process for preparing Type-II composition is comprising the steps of a) preparing a solution of therapeutically effective amount of pharmaceutically acceptable salt of diclofenac in the solvent b) preparing a solution of counter-irritant employing a solublizer, c) optionally dissolving an additional penetration enhancer and antioxidant in the solution obtained in step (b), d) adding under constant stirring, the solution obtained in step (c), to the solution of step (a), and e) adding a sufficient quantity of solvent to make up the volume of the composition up to 100%.

The entire process for the preparation of topical solution of Type-I and II composition is carried out under nitrogen atmosphere.

According to an alternate embodiment of the present invention, the topical solution of salt of diclofenac is prepared by a process comprising (a) preparing a solution of diclofenac diethylamine in propylene glycol with continuous stirring, (b) dissolving a counter irritant menthol in another counter irritant such as methyl salicylate and further dissolving the mixture in ethanol by continuous stirring, (c) adding the solution obtained in the step (b) to the solution obtained in step (a), to produce a clear transparent homogenous topical solution, and (d) making up the volume of the final solution with propylene glycol to obtain the topical solution. The entire process of preparation of topical solution of salt of diclofenac with counter irritant disclosed herein is carried under nitrogen atmosphere.

According to yet another alternate embodiment of the present invention the topical solution of salt of diclofenac is prepared by a process comprising (a) preparing a solution of diclofenac diethylamine in propylene glycol with continuous stirring, (b) dissolving a counter irritant menthol in another counter irritant such as methyl salicylate under continuous stirring and further dissolving the mixture in ethanol by continuous stirring, (c) dissolving an additional penetration enhancer such as oleic acid, isopropyl myristate and/or n-methyl pyrrolidone in the ethanolic solution obtained in step (b), to obtain the solution of counter irritant and additional penetration enhancers in ethanol, (d) adding the solutions obtained in the step (c) under continuous stirring, to the solution obtained in step (a), to produce a clear transparent homogenous topical solution, and (e) making up the volume of the final solution obtained in the step (d) with propylene glycol to obtain the topical solution. The entire process of preparation of topical solution of salt of diclofenac with counter irritant disclosed herein is carried under nitrogen atmosphere.

The various types of topical solution formulations disclosed herein were found to spread uniformly on the skin of a mammal and wherein said topical solution forms a smooth non-greasy film over skin to get penetrated onto to the stratum corneum. The adequate quantity of propylene glycol and humectants such as glycerol and urea ensures that the skin does not get dehydrated when applied. The evaporation of alcohol from the non-aqueous topical solution composition results in formation of a film on the surface of the skin stabilized by the presence of a large amount of propylene glycol solvent employed therein. This ensures the steady penetration of the diclofenac salt dissolved in propylene glycol into the skin of a mammal.

The non-aqueous topical solution composition of the present invention is provided with higher bioavailability than any other dosage form of diethylamine salt of diclofenac known in the art, wherein said composition according to the present invention is prepared without any addition of water.

Further, the pharmaceutically acceptable excipients/additives employed in the present invention are safe and widely used in various dosage forms of pharmaceutically acceptable drugs.

According to the present invention, there is provided a composition having quick penetrating solutions (QPS) of active drugs for topical use, which do not—dehydrate the skin and have optimum viscosity and consistency for uniform spreading over the skin surface.

The viscosity of the topical solution according to the present invention is high enough to facilitate the application and adherence of the topical solution onto the skin of a mammal and is ensured that transdermal penetration is not impaired by its viscosity. The ranges of viscosities are from about 10 to about 50 cps.

EXAMPLE 1

Method of Evaluating Transdermal Absorption of Different Formulations of Pharmaceutically Acceptable Salts of Diclofenac:
Objective of the Study To evaluate the transdermal absorption of pharmaceutically acceptable diethylamine salt of diclofenac topical solutions composition (Type I and Type II) employing three or five healthy human male adult subjects under fasting condition, wherein said evaluation is single or double blind, balanced, randomized, two-treatment, two-sequence, two-period, single dose, crossover bioequivalence study.
Study Design The evaluation of pharmaceutically acceptable salt of diclofenac is carried out in 3 or 5 healthy male volunteers aged between 18 and 40 years. Their medical history, blood and urine examination were done within 15 days prior to participating in the clinical trail study. After scrutinizing the required medical reports by the physician, the human healthy volunteers are certified for their medical fitness to participate in this evaluation study.

These studies were divided in to two different parts, Period I and Period II. The total project for each study was completed in 15 to 20 days from the day of check-in of Period I. Further, there was a gap of at least 7 days between these two periods. During each period subjects were asked to stay in our clinical facility. In each period, subjects were asked to stay at our clinical facility from at least 12 hr before to administration of the study drug to at least 24 hr after administration of the study drug. During this period they were restricted from leaving the clinical trail facility and were asked to adhere to the terms and conditions of the clinical trail procedurals.

Each study consisted of administration of two formulations in two different periods (Period I and Period II). In both the periods, subjects were applied with either one of the formulations, Test or Reference, as per the randomization schedule. The two formulations were applied in appropriate quantities so as to ensure that equal amount of active ingredient was applied. Both the formulations were spread on the entire back side of the human volunteers and gently rubbed for 40 seconds to have equal spreading on to the skin of volunteers.

After applying the formulations or compositions of the said drug in each period, blood samples were collected at different time intervals to evaluate the presence of active ingredient. The blood samples were also withdrawn prior to application of the formulation on to the skin of volunteers. Further, the blood samples were withdrawn after 15 min, 30 min, 45 min, 1 hr, 2 hr, 3 hr, 4 hr, 5 hr, 6 hr, 7 hr, 8 hr, 9 hr, 10 hr, 11 hr, 12 hr, 14 hr and 16 hr followed by application of the formulation of drug in each period.

In order to make the process of collection of blood less painful, a cannula was inserted into the vein of fore arm of the volunteers. The cannula was permanently kept till the completion of the study by injecting 0.5 ml of saline and 0.2 ml of heparin after each sample collection. The first 0.2 ml of heparinized blood was discarded in all subsequent sampling. The blood samples were collected by separate vein puncture where the insertion of cannula was not possible.

During the study, medical officer continuously monitored the volunteers for their vital signs such as oral temperature, sitting blood pressure and radial blood pressure to provide the safety to the volunteers. The monitoring of volunteers is performed at check-in, prior to application of the sample dose and at 2 hr, 4 hr, 8 hr and 12 hr after the application of sample in each period. Further, the clinical examination of the volunteer is performed at the time of check-in and check-out and during the each period as well. All the subjects were questioned for their well being at the time of clinical examinations.

Standardized meals as per the requirements of the study were provided during their participation in the evaluation or study period. Volunteers are provided with magazines, newspapers, viewing television/movies, music, and indoor games like carom, chess and cards during their stay at clinical facility.

All the samples thus collected were immediately centrifuged, plasma was collected in plastic containers (3 ml) and initially stored at −20° C., subsequently at −80° C. until it is being analyzed by High Performance Liquid Chromatography (HPLC) to find the concentration of test or reference drug:

Diclofenac salt was extracted from an aliquot of human plasma using Liquid-Liquid extraction procedure and injected onto the HPLC. Internal standard method was used for quantification of diclofenac. A least square linear regression model (Y=Ax+b, without 0, 0) was used to determine the concentration of the test or reference drug.

It has surprisingly been found that diethylamine salt of diclofenac, a non-aqueous solution composition produces significantly higher transdermal penetration as compared to that of an aqueous solution composition. It was demonstrated by subjecting non-aqueous Formulation No. 11 (comprising diethylamine salt of diclofenac 2.32% w/v, ethanol 10% w/v, propylene glycol, q.s.) and aqueous Formulation 14 (comprising diethylamine salt of diclofenac 2.32% w/v, ethanol 10% w/v, purified water 50% w/v, propylene glycol q.s.,) in their respective bioequivalence study by following said procedure as described above. The results of the said pilot study are as shown in Table 1.

TABLE 1

Single Blind Study

| | Formulation 11 (Non-aqueous, Test) | | | Formulation 14 (Aqueous, Reference) | | |
|---|---|---|---|---|---|---|
| Sr. No. | AUC ng/ml · hr | Cmax ng/ml | Tmax/ Hr | AUC ng/ml · hr | Cmax ng/ml | Tmax/ hr |
| 1. | 1482.47 | 213.45 | 8 | 1572.66 | 206.39 | 7 |
| 2. | 534.83 | 52.42 | 9 | 405.00 | 47.19 | 9 |
| 3. | 1207.00 | 153.08 | 9 | 845.03 | 111.52 | 7 |
| 4 | 480.74 | 55.90 | 11 | 366.10 | 35.54 | 9 |
| 5 | 1123.35 | 139.44 | 11 | 707.81 | 81.81 | 7 |
| Average | 965.66 | 122.86 | 9.60 | 779.32 | 96.49 | 7.80 |

The obtained results in the above study clearly demonstrate that the non aqueous solution composition shows significantly higher transdermal penetration as compared to the aqueous composition. The AUC of the non-aqueous composition is around 24% higher than the corresponding aqueous composition. Further, the Cmax of the non-aqueous composition is around 28% higher as compared to that of non-aqueous solution composition.

In one another bioequivalence study, it was demonstrated that the non-aqueous solution composition showed significantly higher transdermal penetration as compared to that of aqueous solution composition available in the market under the name of Pennsaid (Nuvo Research Inc., Canada). Wherein said aqueous topical solution composition contains 45% w/v of water. The disclosed non-aqueous solution composition (i.e. Formula No. 2) comprising diethylamine salt of diclofenac 2.32% w/v, ethanol 10% w/v, oleic acid 2% w/v, propylene glycol q.s. The results obtained for this study is shown in Table 2.

TABLE 2

| Sr. No. | Formulation No. 2 (Non-aqueous, test) | | | PENNSAID (Aqueous, Reference) | | |
|---|---|---|---|---|---|---|
| | AUC ng/ml · hr | Cmax ng/ml | Tmax/ Hr | AUC ng/ml · hr | Cmax ng/ml | Tmax/ Hr |
| 1 | 312.14 | 75.99 | 7 | 580.55 | 105.39 | 8 |
| 2 | 1014.93 | 245.99 | 9 | 214.51 | 47.58 | 8 |
| 3 | 821.46 | 141.09 | 6 | 557.42 | 82.47 | 7 |
| Average | 716.18 | 154.33 | 7.33 | 450.83 | 78.48 | 7.66 |

A further bioequivalence study was conducted to compare the transdermal penetration of a hydrous gel formulation (e.g. Voveran, Novartis) with a non-aqueous solution composition (Formulation No. 11) prepared in accordance with the present invention comprising diethylamine salt of diclofenac 2.32% w/v, ethanol 10% w/v, propylene glycol, q.s. The results obtained for this study is shown in Table 3.

TABLE 3

| Sr. No. | Formulation No. 11 (Non-aqueous, test) | | | Voveran Gel (Aqueous, Reference) | | |
|---|---|---|---|---|---|---|
| | AUC µg/ml · hr | Cmax µg/ml | Tmax/ hr | AUC µg/ml · hr | Cmax µg/ml | Tmax/ Hr |
| 1. | 2622.6 | 438.01 | 5 | 68.95 | 9.88 | 8 |
| 2. | 1254.9 | 173.84 | 6 | 15.63 | 6.54 | 7 |
| 3. | 2570.8 | 410.59 | 6 | 149.68 | 20.85 | 4 |
| 4. | 1305.2 | 207.14 | 6 | 121.59 | 15.06 | 6 |
| Average | 1938.38 | 307.40 | 5.75 | 88.96 | 13.08 | 6.25 |

It becomes obvious from the above obtained results that the non-aqueous solution composition disclosed in the present invention has much better transdermal penetration as compared to that of market available hydrous gel composition, Voveran Gel.

Another bioequivalence study is conducted to compare the transdermal penetration of a hydrous gel formulation (Voveran) with a non-aqueous solution composition, i.e. Formulation No. 2 comprising diethylamine diclofenac 2.32% w/v, ethanol 10% w/v, oleic acid 2% w/v, propylene glycol q.s. The results obtained for this study is shown in table 4.

TABLE 4

| Sr. No. | Formulation No. 2 (Non-aqueous, test) | | | Voveran Emulgel (Aqueous, Reference) | | |
|---|---|---|---|---|---|---|
| | AUC ng/ml · hr | Cmax ng/ml | Tmax/ hr | AUC ng/ml · hr | Cmax ng/ml | Tmax/ hr |
| 1. | 2100.2 | 341.6 | 6 | BDL* | BDL* | BDL* |
| 2. | 747.3 | 109.99 | 8 | | | |
| 3. | 1833.3 | 278.61 | 7 | | | |
| 4. | 1319.9 | 199.58 | 7 | | | |
| 5. | 1245.2 | 207.06 | 6 | | | |
| Average | 1449.18 | 227.36 | 6.8 | | | |

*BDL—Below Detectable Levels

The results obtained in the above study show that this particular group of volunteers probably had a thick or strong stratum corneum barrier. Wherein, the non-aqueous topical solution composition demonstrated significant transdermal penetration in spite of thick or strong stratum corneum barrier. But aqueous hydro gel formulation (e.g. Voveran Gel) failed to produce the detectable levels of active ingredient drug.

Yet another bioequivalence study was conducted to compare the transdermal penetration of a non-aqueous solution (Formulation No. 1; prepared in accordance with the present invention comprising diethylamine salt of diclofenac 2.32% w/v, methyl salicylate 20% w/v, menthol 10% w/v, ethanol 10% w/v, propylene glycol q.s.) with a cream (Formulation No. 3; comprising diclofenac diethyl amine 1.16% w/v, methyl salicylate 10% w/v, menthol 5% w/v in a cream base,). The results are shown in Table 5.

TABLE 5

| Sr. No. | Formulation No. 1 (Non aqueous, Test) | | | Formulation No. 3 (Aqueous, Reference) | | |
|---|---|---|---|---|---|---|
| | AUC ng/ml/hr | Cmax ng/ml | Tmax/ hr | AUC ng/ml/hr | Cmax ng/ml | Tmax/ Hr |
| 1. | 975.82 | 167.19 | 4 | 532.73 | 75.8 | 7 |
| 2. | 1091.55 | 154.5 | 8 | 415.83 | 53.61 | 6 |
| 3 | 2751.84 | 353.49 | 4 | 985.66 | 89.06 | 9 |
| Average | 1606.40 | 225.06 | 5.33 | 644.74 | 72.82 | 7.33 |

The results obtained for the this study show that the AUC of diclofenac produced by the non-aqueous solution prepared in accordance with the present invention is almost three times that of the conventional cream with the similar active ingredient that are present in the said non-aqueous solution composition.

Although it is known that ethanol enhances transdermal absorption of drugs like diclofenac in aqueous solutions, it was necessary to find out the range of effective ethanol concentrations that would produce optimum transdermal absorption of diclofenac in the novel non aqueous solutions.

Accordingly, additional bioequivalence studies conducted to find out the effects of increased concentration of ethanol in the non-aqueous solution composition. Initially, a non-aqueous solution composition of Formulation No. 4 comprising diethylamine salt of diclofenac 2.32% w/v, ethanol 3% w/v, oleic acid 2% w/v, propylene glycol q.s. was compared with a non-aqueous solution composition of Formulation No. 2 comprising diethylamine salt of diclofenac 2.32% w/v, ethanol 10% w/v, oleic acid 2% w/v, propylene glycol q.s. The results of the study are shown in Table 6

TABLE 6

| Sr. No. | Formulation No. 2 (Non-aqueous) | | | Formulation No. 4 (Non-aqueous) | | |
|---|---|---|---|---|---|---|
| | AUC ng/ml · hr | Cmax ng/ml | Tmax/hr | AUC ng/ml · hr | Cmax ng/ml | Tmax/ hr |
| 1 | 488.62 | 91.7 | 7 | 1002.42 | 122.35 | 12 |
| 2 | 822.44 | 174.76 | 4 | 491.44 | 66.86 | 6 |
| 3 | 736.81 | 199.84 | 4 | 431.96 | 73.95 | 5 |
| 4 | 808.99 | 113.51 | 7 | 963.4 | 128.69 | 8 |
| 5 | 1834.76 | 295.72 | 6 | 575.19 | 69.99 | 7 |
| Average | 938.32 | 175.10 | 5.6 | 692.88 | 92.36 | 7.6 |

The results clearly demonstrate that reducing the concentration of ethanol from 10% w/v to 3% w/v would reduce the transdermal penetration significantly. Hence, the concentration of ethanol is directly related to the transdermal penetration topical solution of said composition.

Further, bioequivalence study was conducted with the objective of finding the relationship between increased concentration of ethanol and transdermal penetration of topical solution composition containing salts of diclofenac. A non-aqueous topical solution composition of Formulation No. 9 comprising diclofenac diethyl ammonium 2.32% w/v, ethanol 20% w/v, oleic acid 2% w/v, propylene glycol q.s. was compared to that of non-aqueous topical solution composition of Formulation No. 2 comprising diclofenac diethyl ammonium 2.32% w/v, ethanol 10% w/v, oleic acid 2% w/v, propylene glycol q.s. The results of this bioequivalence study are shown in Table 7.

TABLE 7

| | Formulation No. 2 (Non-aqueous) | | | Formulation No. 9 (Non-aqueous) | | |
|---|---|---|---|---|---|---|
| Sr. No. | AUC ng/ml/hr | Cmax ng/ml | Tmax/ hr | AUC ng/ml/hr | Cmax ng/ml | Tmax/ hr |
| 1 | 1053.32 | 148.53 | 7 | 1429.95 | 260.73 | 7 |
| 2 | 3063.59 | 527.61 | 4 | 3702.53 | 767.56 | 4 |
| Average | 2058.45 | 225.38 | 5.5 | 2566.24 | 514.14 | 5.5 |

The above revealed results definitely demonstrate that increasing the concentration of ethanol from 10% w/v to 20% w/v would increase the transdermal penetration of topical solution composition of salt of diclofenac.

Further objective of the bioequivalence study was discovering whether additional increase in the concentration of ethanol would benefit the transdermal penetration topical solution of salt of diclofenac or not. The bioequivalence study results of non-aqueous topical solution composition of Formulation No. 9 comprising Diclofenac diethyl ammonium 2.32% w/v, ethanol 20% w/v, oleic acid 2% w/v, propylene glycol q.s. is compared with that of non-aqueous topical solution composition of Formulation No. 10 comprising Diclofenac diethyl ammonium 2.32% w/v, ethanol 30% w/v, oleic acid 2% w/v, propylene glycol q.s.

The obtained results for this bioequivalence study has clearly indicated that increasing the concentration of ethanol from 20% to 30% does not produce any increase in their transdermal penetration of topical solution composition. The results of the study are shown in Table 8.

TABLE 8

| | Formulation No. 9 (Non-aqueous) | | | Formulation No. 10 (Non-aqueous) | | |
|---|---|---|---|---|---|---|
| Sr. No. | AUC ng/ml/hr | Cmax ng/ml | Tmax/ hr | AUC ng/ml/hr | Cmax ng/ml | Tmax/ hr |
| 1 | 1246.82 | 187.6 | 5 | 839.23 | 139.5 | 7 |
| 2 | 2046.85 | 373.36 | 4 | 942.72 | 140.88 | 7 |
| 3 | 1586.42 | 304.44 | 6 | 3002.02 | 577.72 | 5 |
| 4 | 944.0 | 120.02 | 7 | 827.72 | 129.3 | 8 |
| 5 | 669.32 | 99.51 | 6 | 765.25 | 93.04 | 8 |
| Average | 1298.68 | 216.98 | 5.6 | 1275.38 | 216.08 | 7 |

Undoubtedly, numerous variations and modifications of the invention will become readily apparent to those familiar with transdermal drug and medication delivery systems. Accordingly, the scope of the invention should not be construed as limited to the specific examples depicted and described, but rather is defined in the claims appended hereto.

I claim:

1. A novel composition comprising:
    an effective amount of pharmaceutically acceptable salt of diclofenac in the range of 1.16% to 5% w/v;
    a penetration enhancer and solubilizer in the range of 10 to 20% v/v of a lower chain alcohol;
    a solvent in an amount greater than 75% and selected from propylene glycol, glycofurol and mixtures thereof; and
    an additional penetration enhancer in the range of 1 to 5% w/v, and selected from the group consisting of
        oleic acid,
        N-methyl-pyrrolidone (NMP),
        2-methyl-pyrrolidone, and
        1-methyl-pyrrolidone;
    wherein the composition is a non-aqueous topical solution.

2. The composition according to claim 1, consisting essentially of the pharmaceutically acceptable salt of diclofenac, the additional penetration enhancer and solubilizer, the solvent, and the additional penetration enhancer.

3. The composition according to claim 1, wherein the solvent is greater than or equal to 60%.

\* \* \* \* \*